(12) United States Patent
Humbert et al.

(10) Patent No.: US 9,188,540 B2
(45) Date of Patent: Nov. 17, 2015

(54) INTEGRATED CIRCUIT AND MANUFACTURING METHOD

(71) Applicant: NXP B.V., Eindhoven (NL)

(72) Inventors: Aurelie Humbert, Brussels (BE); Roel Daamen, Herkenbosch (NL); Youri Victorovitch Ponomarev, Leuven (BE)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 14/147,214

(22) Filed: Jan. 3, 2014

(65) Prior Publication Data

US 2014/0191348 A1 Jul. 10, 2014

(30) Foreign Application Priority Data

Jan. 7, 2013 (EP) .................................... 13150418

(51) Int. Cl.
*H01L 31/02* (2006.01)
*G01N 21/76* (2006.01)
*G01N 29/02* (2006.01)
*G01N 29/036* (2006.01)
*G01N 33/00* (2006.01)

(52) U.S. Cl.
CPC ............ *G01N 21/766* (2013.01); *G01N 29/022* (2013.01); *G01N 29/036* (2013.01); *G01N 33/004* (2013.01); *H01L 31/02* (2013.01); *G01N 2291/021* (2013.01); *G01N 2291/0256* (2013.01); *G01N 2291/02809* (2013.01); *G01N 2291/0427* (2013.01)

(58) Field of Classification Search
CPC .... H01L 31/02; G01N 27/129; G01N 27/407; G01N 27/4074; G01N 33/00; G01N 33/0009
USPC ....... 257/414, 431, 432, E29.166; 438/48, 49
See application file for complete search history.

(56) References Cited

FOREIGN PATENT DOCUMENTS

EP 2 333 532 A1 6/2011

OTHER PUBLICATIONS

B. Lamprecht et al, "Integrated waveguide sensor utilizing organic photodiodes", Phys. Status Solidi RRL, 2011.*
Arshak, K. et al., "A Review of Gas Sensors Employed in Electronic Nose Applications", Sensor Review, vol. 2, No. 2, pp. 181-198 (2004.
Liu, Y. et al. "Sitchable Surfactants", Science, vol. 313, No. 5789, pp. 958-960 (Aug. 18, 2006).
Liu, Y. et al. "Fluorescent Chemosensor for Detection and Quantitation of Carbon Dioxide Gas", J. of the Amer. Chemical Society, vol. 132, No. 132, pp. 13951-13953 (2006).
Bai, H. et al., "Gas Sensors Based on Conducting Polymers." Sensors 7, pp. 267-307 (2007).

(Continued)

*Primary Examiner* — Daniel Whalen
*Assistant Examiner* — Suberr Chi

(57) ABSTRACT

Disclosed is an integrated circuit comprising a substrate (10); and an optical $CO_2$ sensor comprising: first and second light sensors (12, 12') on said substrate, said second light sensor being spatially separated from the first light sensor; and a layer portion (14) including an organic compound comprising at least one amine or amidine functional group over the first light sensor; wherein said integrated circuit further comprises a signal processor (16) coupled to the first and second light sensor for determining a difference in the respective outputs of the first and second light sensor. An electronic device comprising such a sensor and a method of manufacturing such an IC are also disclosed.

11 Claims, 5 Drawing Sheets

(56) References Cited

OTHER PUBLICATIONS

Dibenedetto, A. et al., "Hybrid Materials for $CO_2$ Uptake from Simulated Flue Gases: Xerogels Containing Diamines", ChemSusChem, Special Issue: 2nd EuCheMS Chemistry Congress, vol. 1, No. 8-9, pp. 742-745 (Sep. 1, 2008).

Darwish, T. A. et al., "Spiropyran-Amidine: A Molecular Canary for Visual Detection of Carbon Dioxide Gas", Chem. Eur. J., vol. 17, pp. 11399-11404 (2011).

Ali, R. et al. "Optical Sensing Scheme for Carbon Dioxide Using a Solvatochromic Probe", Anal. Chem., No. 83, pp. 2846-2851 (2011).

NRL Report 6047, "Filament-winding plastics Part 1—Molecular Structure and Tensile Properties" of Mar. 16, 1964, 12 pgs., retrieved from the Internet Aug. 7, 2012 at: https://torpedo.nrl.navy.mil/tu/ps/pdf/pdf_loader?dsn=7590632.

Extended European Search Report for EP Patent Appln. No. 13150418.5 (Jun. 10, 2013).

\* cited by examiner

US 9,188,540 B2

INTEGRATED CIRCUIT AND MANUFACTURING METHOD

CROSS-REFERENCE TO RELATED APPLICATIONS

This application claims the priority under 35 U.S.C. §119 of European patent application no. 13150418.5, filed on Jan. 7, 2013, the contents of which are incorporated by reference herein.

FIELD OF THE INVENTION

The present invention relates to an integrated circuit (IC) comprising a $CO_2$ sensor.

The present invention further relates to a method of manufacturing such an IC.

BACKGROUND OF THE INVENTION

Nowadays, integrated circuits (ICs) may comprise a plethora of sensors, such as gas sensors, relative humidity (RH) sensors, specific analyte detection sensors, and so on. Such sensors may be included in the IC design for a number of reasons.

For instance, a gas sensor may be included in an IC to detect a change in the ambient conditions of a product tagged with the chip such that product quality control can be achieved by monitoring the sensor readings of the chip. This can for instance be used to accurately predict the remaining shelf life of the product, e.g. perishable food stuff. The gas sensor may for instance be adapted to determine changes in the $CO_2$ content of the ambient atmosphere. Alternatively, the gas sensor may be used to detect changes in the gas composition of larger environment such as buildings or may be used in medical application domains, e.g. in breathing apparatuses.

With the ongoing diversification of electronic devices or electronic information gathering such as by RF tags on packaged articles, it is often desirable to include different types of sensors in a single IC. For instance, the detection of other environmental parameters, for instance temperature and humidity such as for HVAC (heating, ventilation and air conditioning) control in buildings and cars, are particularly desirable in certain application domains. In addition, sensing of analytes of interest, e.g. $CO_2$, may be desirable in such application domains. However, it is difficult to manufacture $CO_2$ sensors having the desired sensitivity in a cost-effective manner. In particular, impedometric $CO_2$ sensors, i.e. sensors based on measuring the change in the impedance of a material based on its exposure to $CO_2$, suffer from relatively poor sensitivity.

Multiple sensor ICs are known per se. However, most solutions are based on a system comprising multiple discrete sensors, which makes the system bulky and rather expensive. Also, the manufacturing process can be rather complex, especially when sensors with high sensitivity are to be included in the design. This negatively impacts on production yield and pushes up the price of the known good products.

SUMMARY OF THE INVENTION

The present invention seeks to provide a compact IC comprising a $CO_2$ sensor that has good sensitivity and can be manufactured in a cost-effective manner.

The present invention further seeks to provide a method for manufacturing such an IC in a cost-effective manner.

According to an aspect of the present invention, there is provided an integrated circuit comprising a substrate; and an optical $CO_2$ sensor comprising first and second light sensors on said substrate, said second light sensor being spatially separated from the first light sensor; and a layer portion including an organic compound comprising at least one amine or amidine functional group for reacting with $CO_2$ over the first light sensor; wherein said integrated circuit further comprises a signal processor coupled to the first and second light sensor for determining a difference in the respective outputs of the first and second light sensor.

The present invention is based on the realization that organic compounds such as amines, e.g. meso-aromatic diamines, or amidine-based organic compounds, which have the ability to cloud or otherwise alter their transmissivity including changing their colour upon exposure to $CO_2$, can be used to determine the concentration of $CO_2$ in a medium to which the organic compound is exposed. To this end, the provision of light sensor having the organic compound in its light path and a reference light sensor means that a $CO_2$-induced change in the difference of the output signals of both light sensors caused by the induced change in transmittance through the organic compound containing layer portion can be used to accurately determine the $CO_2$ concentration.

At this point it is noted that it is known per se that (di)amine compounds can cloud its host materials upon exposure to $CO_2$. For instance, in NRL Report 6047 "Filament-winding plastics Part 1—Molecular Structure and Tensile Properties" of Mar. 16, 1964 and retrieved from the Internet: https://torpedo.nrl.navy.mil/tu/ps/pdf/pdf_loader?dsn=7590632 on Tuesday 7 Aug. 2012 it is disclosed that m-xylylene diamine and an epoxy resin containing it have a tendency to cloud as the amine absorbs carbon dioxide from the atmosphere. Moreover, A. Dibenedetto et al. in ChemSusChem, Special Issue: 2nd EuCheMS Chemistry Congress, Volume 1, Issue 8-9, pages 742-745, Sep. 1, 2008 disclose the reversible uptake of $CO_2$ from simulated flue gases by mono- and disilyl amines, either in their free form, as organic (wet) solutions, or as xerogels.

Liu et al. in Science, Vol. 313 (2006) pages 958-960 disclose a surfactant including amidine functional group that can be switched upon exposure to $CO_2$ to a clouded amidinium bicarbonate salt.

Darwish et al. in Chem. Eur. J. 17 (2011), pages 11399-11404 disclose a spiropyran amidine that exhibits a colour change upon formation of the amidinium bicarbonate salt following reaction with $CO_2$.

However, none of these prior art citations have come to the realization that the change in transmissivity at a defined wavelength of such organic compounds caused by the clouding or colour change induced by the reaction of the organic compounds with $CO_2$ may be used to determine $CO_2$ levels.

In an embodiment, the IC may also comprise a further sensor comprising a pair of electrodes separated by a gas or moisture sensitive material. For instance, the integrated circuit may comprise an interconnect structure over the substrate and at least one passivation layer over the interconnect structure, said layer portion and said further sensor being at least partially located on the passivation layer. This has the advantage that parts of the processing steps of manufacturing the further sensor can also be used to further functionalize the optical $CO_2$ sensor.

In an embodiment, the $CO_2$ sensor comprises a further layer portion of the gas or moisture-sensitive material over the first light sensor, said organic compound containing layer portion at least partially covering the further layer portion. In this embodiment, the further layer portion of the sensitive material is used as a wavelength filter for the first light sensor, which has the advantage that such a filter can be formed over the first light sensor without requiring additional processing steps. This is particularly advantageous if the first and second light sensors are photosensitive diodes, such as photo-sensitive Si diodes. Si diodes in general have little wavelength selectivity and detect a rather wide spectrum that can include UV, visible as well as IR irradiation up to 1100 nm. Significant amount of literature exists on how it is possible to vary the sensitivity of the photodiodes to a given part of the spectrum using different diffusion depths of the dopants to form the diode junctions, formation of vertically-stacked diodes, as well as package- or casing-level filters applications. These methods, however, either do not deliver appropriate selectivity to the desired parts of the spectrum and require a significant amount of signal post-processing, or only allow a single part of the spectrum to be sensed by the diode.

The moisture sensitive material may comprise a polymer such as a polymer selected from the group consisting of polyacrylates, polymethacrylates, polyimides, polyamides, polyamines, polypyridines, polycarbonates, polyacetates, polystyrenes, polyacetylenes, polyanilines, polypyrroles, polythiophenes, poly(phenyl vinylene) and derivatives thereof. Polyimide is a particularly preferred polymer as this polymer exhibits optical properties that can be tuned by controlling its curing temperature as for instance has been disclosed in J. Chem. Phys., 1993, Vol. 38, page 3445.

At least the further layer portion of the moisture sensitive material may further comprise a dye to further tune the filter properties of the further layer portion. Such a dye may be dissolved or otherwise dispersed through the moisture sensitive material, or may be chemically bound to the moisture sensitive material, e.g. by covalent, ionic or VanderWaals bonding of the dye to a suitable polymer. As only small amounts of dye need adding, the moisture sensitivity of the material remains substantially unaltered. For this reason, any suitable dye may be used as the only consideration is the desired absorption spectrum of the selected dye, which is well-documented for numerous dyes, such that it is practically unfeasible to include particular examples of such dyes in the present application.

The layer portion may comprise the organic compound immobilized in a further polymer. The organic compound may be dissolved or otherwise dispersed through the further polymer, e.g. encapsulated in a further polymer matrix, or may be chemically bound to the further polymer, e.g. by covalent, ionic or VanderWaals bonding of the organic compound to a suitable polymer.

In an alternative embodiment, the IC may comprise a polymer well structure surrounding the first light sensor, wherein the organic compound is contained in the polymer well structure. This has the advantage that the organic compound may be deposited within the well structure as a liquid, in which case the well may be sealed off with a $CO_2$-permeable membrane. Such well structures are known per se; see e.g. U.S. Pat. No. 5,376,255.

The IC of the present invention may be suitably integrated in devices such as electronic devices, vehicles and so on, as well as in the packaging of packaged items, in which case the IC may for instance be a RF-ID chip for monitoring environmental conditions of the packaged item, which monitoring data may be relayed to a control center via the RF link.

In accordance with another aspect of the present invention, there is provided a method of manufacturing an integrated circuit comprising an optical $CO_2$ sensor, comprising providing a substrate comprising first and second light sensor spatially separated from each other and a signal processor coupled to the first and second light sensor for determining a difference in the respective outputs of the first and second light sensor and forming a layer portion including an organic compound comprising an amine or amidine functional group over the first light sensor. In this manner, a sensitive $CO_2$ sensor can be produced in a cost-effective manner.

In a preferred embodiment, the method further comprises forming an interconnect structure over the substrate and forming at least one passivation layer over the interconnect structure, said passivation layer including a first area over the at least one light sensor; wherein the step of forming the layer portion comprising forming the layer portion in the first area. In this manner, the IC is protected against environmental influences, e.g. moisture ingress, thus increasing the robustness of the IC.

The method may further comprise forming a further sensor at least partially on the at least one passivation layer by forming a pair of electrodes on a further area of the at least one passivation layer; depositing a gas or moisture sensitive layer over the at least one passivation layer including the pair of electrodes; and patterning the gas or moisture sensitive layer such that the gas or moisture sensitive layer remains in the first and further areas; wherein the step of forming the layer portion comprises forming the layer portion at least partially over the portion of the gas or moisture sensitive layer portion remaining in the first area. Because the patterning of the gas or moisture sensitive layer is usually necessary anyway, the insight of the present invention that one or more filters of parts of the EM spectrum can be provided by also using the gas or moisture sensitive layer material for this purpose means that such filters can be provided in the same patterning step, such that the inclusion of such filters is provided without adding to the complexity of the manufacturing process, i.e. without requiring additional processing steps, which renders the method of the present invention particularly cost effective whilst at the same time not negatively affecting production yield.

In case the gas or moisture sensitive layer material is a polymer layer selected from the group consisting of polyacrylates, polymethacrylates, polyimides, polyamides, polyamines, polypyridines, polycarbonates, polyacetates and polystyrenes, polyacetylenes, polyanilines, polypyrroles, polythiophenes, poly(phenyl vinylene) and derivatives thereof, the step of depositing a moisture sensitive layer may be achieved by spin-coating.

A dye may be included in at least the portion of the gas or moisture sensitive layer over the first area to tune the properties of the filter. Such a dye may be chemically bound to the gas or moisture sensitive layer material, e.g. covalently bound, ionically bound or bound by VanderWaals forces.

In a further embodiment, a second further portion of the gas or moisture sensitive layer may also be provided over the second area, i.e. in the light path of the reference light sensor such that the first and second light sensors are exposed to the same part of the electromagnetic spectrum.

BRIEF DESCRIPTION OF THE EMBODIMENTS

Embodiments of the invention are described in more detail and by way of non-limiting examples with reference to the accompanying drawings, wherein:

FIG. 1 schematically depicts an IC according to an embodiment of the present invention;

FIG. 2A schematically depicts the measurement principle of an IC according to an embodiment of the present invention;

FIG. 2B is an image demonstrating the clouding of a diamine containing liquid upon exposure to $CO_2$;

FIG. 3 schematically depicts an IC manufacturing method according to an embodiment of the present invention;

FIG. 4 schematically depicts a reaction scheme that may be used in an embodiment of the present invention;

DETAILED DESCRIPTION OF THE DRAWINGS

Figure 1:
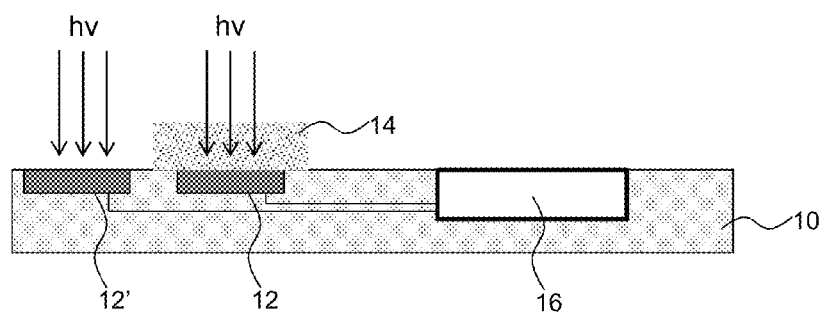

It should be understood that the Figures are merely schematic and are not drawn to scale. It should also be understood that the same reference numerals are used throughout the Figures to indicate the same or similar parts.

FIG. 1 schematically depicts an IC comprising an optical $CO_2$ sensor according to the general inventive concept of the present invention. A substrate 10, .g. a Si substrate, a SiGe substrate, a silicon on insulator (SOI) substrate and so on, which typically comprises a plurality of circuit elements such as transistors, diodes, and so on, is provided with a first photosensitive element 12 and a second photosensitive element 12' spatially separated from the first photosensitive element 12. In FIG. 1, the first photosensitive element 12 and the second photosensitive element 12' are laterally separated by way of non-limiting example only. It is equally feasible that the first photosensitive element 12 and the second photosensitive element 12' are vertically separated, e.g. in the case of a vertically stacked diode comprising the photosensitive element 12 on top of the second photosensitive element 12' or vice versa.

The first photosensitive element 12 is covered by a layer portion 14 that includes an organic compound comprising at least one amine (e.g. a diamine) or amidine functional group. The layer portion 14 has a transmittance to a part of interest of the electromagnetic (EM) spectrum, e.g. visible light, which is a function of the amount of $CO_2$ that is bound to the diamine compound in the layer portion 14.

In an embodiment, the reaction of the organic compound with $CO_2$ in the layer portion 14 causes a degree of clouding in the otherwise substantially transparent layer portion 14. This reduces the amount of light that is transmitted through the layer portion 14.

In an alternative embodiment, the reaction of the organic compound with $CO_2$ in the layer portion 14 causes a change in the absorbance spectrum of the organic compound, which may be detected by the photosensitive element 12 by a change in the intensity in light of a wavelength affected by such a change.

Any suitable organic compound including at least one amine or amidine functional group that causes a transmissivity change at a defined wavelength upon reaction with $CO_2$, e.g. through clouding or a change in its absorbance spectrum, may be used.

The organic compound may be immobilized in the layer portion 14 in any suitable manner. For instance, the organic compound may be applied onto the substrate 10 in a solvent, which is subsequently evaporated to leave behind the organic compound in a neat form, e.g. a gel or solid. Alternatively, the organic compound, either in neat form or dissolved in a suitable solvent, e.g. an alcohol having negligible vapour pressure at room temperature (25° C.), such as oleyl alcohol, may be encapsulated in a polymer matrix, which may be formed by a curing reaction (chemically cross-linked polymers) or by self-assembly (physically cross-linked polymers).

In yet another embodiment, the organic compound may be placed inside a limiting structure such as a polymer well structure formed on top of the passivation or metallization stack of the IC. Such a well structure may for instance comprise a polyimide well structure comprising an inner well in which the organic compound is placed and an outer well in which a gas permeable membrane covering the inner well is anchored. Such well structures and membranes are well known per se in the art, e.g. from the field of bodily fluid sensors. For instance, an example of a gas sensor utilizing such a well structure is disclosed in U.S. Pat. No. 5,376,255. An advantage of this embodiment is that the organic compound may be placed inside the inner well in liquid form, e.g. neat or dissolved in a suitable solvent, such that no separate immobilization steps are required.

In an embodiment, the well structure is placed over the first photosensitive element 12, with the second photosensitive element 12' not comprising such a well structure. In an alternative embodiment, the first photosensitive element 12 and the second photosensitive element 12' each comprise separate well structures, in which the well structure over the second photosensitive element 12' is filled with a reference liquid, such as a solvent used to dissolve the organic compound in the well structure over the first photosensitive element 12.

In FIG. 1, the layer portion 14 is placed in direct contact with the first photosensitive element 12, e.g. a photodiode, by way of non-limiting example only. Alternatively, one or more layers (not shown) that are at least partly transparent to the part of the EM spectrum of interest may be present in between the photosensitive element 12 and the layer portion 14. For instance, the one or more layers may define a metallization stack of the IC for interconnecting the various circuit elements on the substrate 10 and for providing external connections to the circuit elements.

The second photosensitive element 12' acts as a reference photosensitive element, and is included in the design to filter out variations in the incident light levels to which the IC is exposed. A signal processing circuit 16 is also present in or on the substrate 10, which is connected to the respective outputs of the first photosensitive element 12 and the second photosensitive element 12'. Although in FIG. 1 these connections are shown as being embedded in the substrate 10, it should be understood that this is for the sake of clarity only. It is for instance equally feasible that such connections are routed over the substrate 10, e.g. form part of the aforementioned metallization stack (not shown).

The signal processing circuit 16 is adapted to calculate a difference between the light intensities measured by the first photosensitive element 12 and the second photosensitive element 12' respectively and to correlate this difference to a $CO_2$ level. To this end, the signal processing circuit 16 may comprise or have access to a memory circuit (not shown), e.g. a look-up table, in which a measured difference in light intensity is correlated to a predetermined $CO_2$ level, such that the signal processor can retrieve the appropriate $CO_2$ level from the memory circuit.

In an embodiment, the light intensities are measured at a selected wavelength, which is for instance advantageous in case the organic compound exhibits a change in its absorbance spectrum upon reaction with $CO_2$, as for instance is the case for the spiropyran amidine compound as disclosed by Darwish et al.

In an embodiment, the signal processing circuit 16 is adapted to determine a change in the ratio of the light intensities of the first photosensitive element 12 and the second photosensitive element 12', e.g.:

$$R=[I(\mathbf{12})/I(\mathbf{12'})]$$

In which R is the dimensionless ratio and I(12) and I(12') are the values of the voltage or current signals obtained from the first photosensitive element 12 and the second photosensitive element 12' respectively. The value of the ratio can be correlated to a $CO_2$ level as previously explained.

In the absence of $CO_2$ in the layer portion 14, the ratio R may be constant over a wide range of light intensities. Alternatively, the ratio R may be a function of the light intensity, in which case the above equation may be amended to:

$$R[(I(\mathbf{12})]=[I(\mathbf{12})/I(\mathbf{12'})]$$

In this embodiment, the memory circuit will store N look-up tables for the N different values of the ratio R, with N being a positive integer of at least 2. Other suitable algorithms to be implemented by the signal processing circuit 16 will be immediately apparent to the skilled person.

The photosensitive elements 12 and 12' may be realized in any suitable manner, e.g. photosensitive diodes, which may be single diodes, vertically stacked diodes and so on. In case of a vertically stacked diode, the substrate 10 is usually at least partially transparent such that the bottom diode can be illuminated through the substrate. This may for instance be achieved by thinning the substrate to a thickness such that it becomes as at least partially transparent.

Figure 2A:
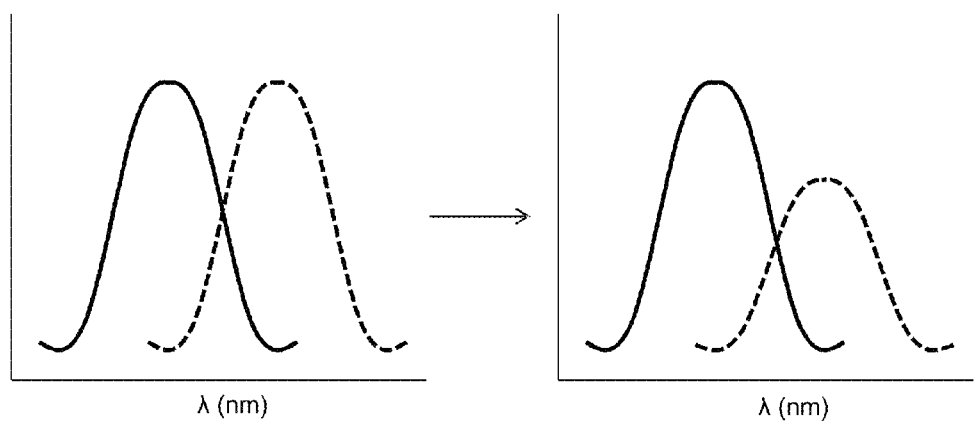

FIG. 2A schematically depicts the operating principle of the $CO_2$ sensor of the present invention. The dashed line depicts the response or sensitivity of the $CO_2$-sensitive photosensitive element 12 to a part of the EM spectrum, whereas the solid line depicts the response or sensitivity of the reference photosensitive element 12' to the same part of the EM spectrum, e.g. a selected wavelength or wavelength range. The response curves have been horizontally displaced for the sake of clarity; it should be understood that normally the maximum response of the respective curves substantially coincide if the photosensitive elements 12 and 12' are of the same design.

The left hand pane depicts the response of the photosensitive elements 12 and 12' in the absence of $CO_2$ and the right hand pane depicts the response of the photosensitive elements 12 and 12' after the diamine compound in the layer portion 14 has reacted with ambient $CO_2$, thus causing clouding or a change in the absorbance spectrum of the layer portion 14, which alters, e.g. reduces, the transmittance of the layer portion 14 to the selected part of the EM spectrum. This increases the difference in the output signals produced by the photosensitive elements 12 and 12', which can be converted by the signal processing circuit 16 into a detected level of $CO_2$.

Figure 2B:
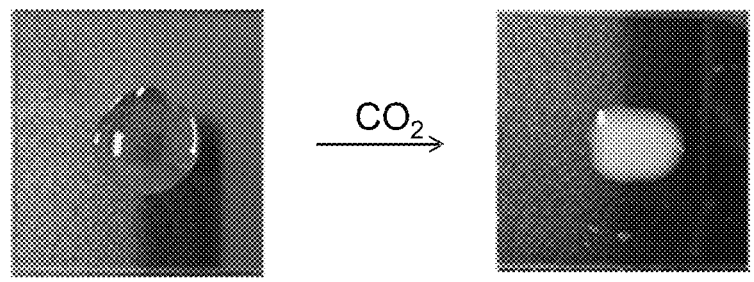

As shown in FIG. 2B, a droplet of oleyl alcohol comprising 5% by weight of a meso-diamine ((1R, 2S)-1,2-diphenyl-1, 2-ethanediamine) changes within 5 minutes from a clear to a milky, clouded appearance upon exposing the droplet to a $CO_2$-flush, thus demonstrating the ability of diamine compounds to cloud a host material upon a binding reaction with $CO_2$.

Figure 3:
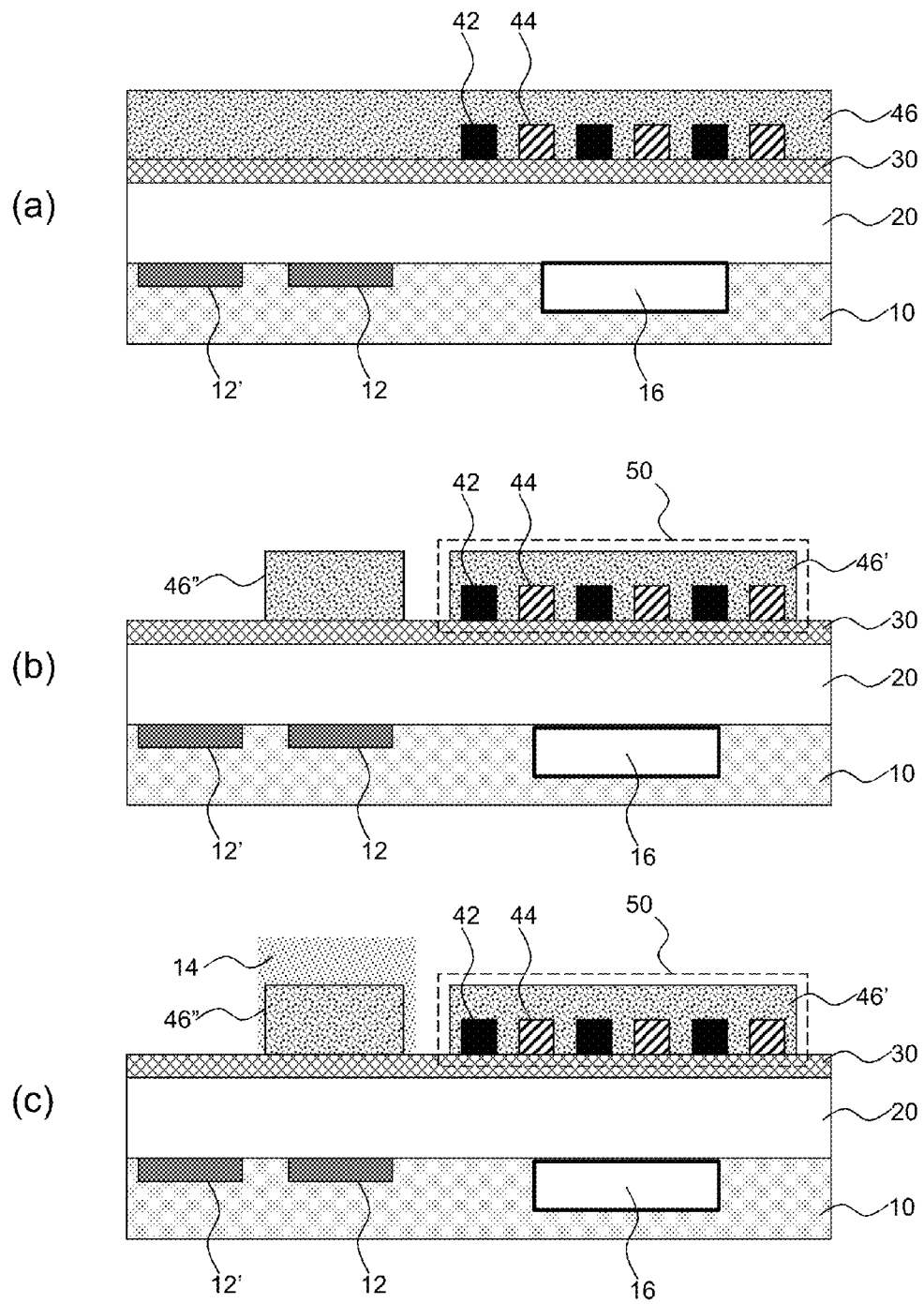

FIG. 3 schematically depicts a method of manufacturing an IC in accordance with an embodiment of the present invention. The IC of the present invention may be provided using any suitable manufacturing technology, such as CMOS, silicon-on-insulator and SiGe technologies. As shown in FIG. 3(*a*), there is provided an IC that comprises a substrate 10, e.g. a Si substrate, a SiGe substrate, a silicon on insulator (SOI) substrate and so on, which typically comprises a plurality of circuit elements such as transistors, diodes, and so on, combinations of which from circuits including the signal processing circuit 16. These may be analog or digital circuits. The manner in which this substrate provided is not particularly limited.

Any suitable manufacturing method may be employed to provide such a substrate. As such methods are numerous and commonplace, this will not be further explained for the sake of brevity only. It should further be understood that the present invention is not limited to specific types of ICs. The present invention may be included in any suitable IC, including digital ICs, analog ICs and mixed signal ICs.

A first photosensitive element 12 and a second photosensitive element 12' acting as a reference light sensor as previously explained are formed on the substrate 10. The photosensitive elements 12 and 12' may take any suitable shape, e.g. photosensitive diodes, which may be single diodes, vertically stacked diodes and so on. In case of a vertically stacked diode, the substrate 10 is usually at least partially transparent such that the bottom diode can be illuminated through the substrate. This may for instance be achieved by thinning the substrate to a thickness such that it becomes as at least partially transparent. The photosensitive elements 12 and 12' form part of the $CO_2$ sensor of the IC and are typically connected to signal processing circuit 16.

The interconnections between the circuit elements in the substrate 10 to define the circuits are typically provided by a metallization layer or layer stack 20, which by way of non-limiting example may comprise a plurality of patterned metal layers separated by dielectric layers. Any suitable number of metal layers and dielectric layers may be present. Metal portions in different metal layers may be conductively interconnected by one or more vias formed in a dielectric layer in between the respective portions of the metal layers. Any suitable material may be used to form the metallization stack 20, such as Ti, TiN, Al, Cu and combinations thereof to define the metal layers and silicon oxide, silicon nitride, low-k dielectrics and other dielectric materials as well as combinations thereof to form the dielectric layers.

Each layer of the metallization stack 20 may in fact comprise a stack of layers, as is common design practice in contemporary semiconductor technologies such as sub-micron CMOS technologies. Any suitable manufacturing method may be employed to provide such an interconnect structure. As such methods are numerous and commonplace, this will not be further explained for the sake of brevity only.

A passivation layer 30 is typically provided over the metallization stack 20 to protect the interconnect structure and the substrate 10 from damage, e.g. from exposure to excess moisture. Again, any suitable passivation layer 30 may be employed. Non-limiting examples of suitable materials for such a passivation structure include dielectric materials such as $SiO_2$, $Si_3N_4$, low-k dielectrics and combinations thereof. In addition, the passivation structure may further comprise a moisture barrier material such $Ta_2O_5$. Preferably, the passivation layer 30 is a layer stack comprising one or more layers of a dielectric material, which may be formed in any suitable manner. As such methods are numerous and commonplace, this will not be further explained for the sake of brevity only.

It will be clear that the metallization layer 20 and the passivation layer 30 are at least partially transparent to the part of the electromagnetic (EM) spectrum of interest, such that this light can reach the photosensitive element 12.

A first electrode 42 and a second electrode 44 are formed on top of the passivation layer 30, which preferably is planarized prior to the formation of these electrodes. A suitable planarization method is chemical mechanical polishing. The electrodes 42 and 44 may be formed in any suitable manner, e.g. by depositing a metal layer on top of the passivation layer 30 and patterning this metal layer to obtain the first electrode 42 and the second electrode 44. In FIG. 3(a), the first electrode 42 and the second electrode 44 are shown as interdigitated electrodes by way of non-limiting example only. It will be appreciated that any suitable electrode design may be contemplated. Any suitable metal may be used for the electrodes. Preferably, the first electrode 42 and the second electrode 44 are formed of a metal that is also used to form the metal interconnects in the metallization layer 20 as this means that the electrodes may be formed by processes that are already available in the manufacturing process of the IC.

The electrodes 42 and 44 form the electrodes of a capacitive or resistive gas or moisture sensor on top of the passivation layer of the IC. A non-limiting example of such a type of sensor is described in more detail in European patent application EP09166518.2. The electrodes 42 and 44 may be conductively connected for reading out purposes in any suitable manner. The electrodes 42 and 44 may be connected to circuitry on the substrate of the IC via the metallization stack 20, in which case respective electrically conductive portions extend from the electrodes 42 and 44 to different metal portions of the metallization stack 20 through the passivation layer 30. Alternatively, the passivation layer 30 may carry respective contact pads (not shown) to which the electrodes 42 and 44 are conductively connected such that the gas or moisture sensor may be read out externally by contacting these contact pads.

According to an embodiment of the present invention, a gas or moisture sensitive layer 46 is formed over the passivation layer 20 including the first electrode 42 and the second electrode 44. In the context of the present invention, a gas or moisture sensitive material is a material that has electrical properties, e.g. conductive, resistive and/or capacitive properties that are a function of the gas or moisture content in the material. For instance, in case of a capacitive moisture sensor, the moisture sensitive material is a material that has a dielectric constant that depends on its moisture content, such that the moisture content can be determined by determining the capacitance of the sensor.

Alternatively, an impedance measurement across the portion of the gas or moisture sensitive layer 46 in between the electrodes 42 and 44 can be performed to determine the gas levels in or relative humidity of the environment in which the IC is placed. Such a measurement could also be used to determine if the IC has been exposed to excessive humidity levels, e.g. has been immersed in water.

It will be understood that in case of a moisture sensor on the passivation layer 30, this sensor may be used as a relative humidity sensor or as a liquid immersion sensor instead.

Any suitable gas or moisture sensitive material may be used. For example, the moisture sensitive material may be a polymer selected from the group consisting of polyacrylates, polymethacrylates, polyimides, polyamides, polyamines, polypyridines, polycarbonates, polyacetates and polystyrenes and derivatives thereof. Polyimide is particularly preferred. In case of the layer 46 comprising such a polymer, the layer 46 may for instance be formed by spin-coating or any other suitable polymer deposition technique.

Alternatively, polymers such as polyacetylenes, polyanilines, polypyrroles, polythiophenes, poly(phenyl vinylene) and derivatives thereof may be used, in particular if gases other than gaseous water (moisture) are to be detected. It is for instance known per se that several conductive polymers such as polypyrrole, polyaniline, polythiophene and their derivatives have successfully been used as gas sensitive layers in gas sensors. It is also known per se that for instance polythiophene and poly(dodecylthiophene) sensors can have sensitivities in the range of 0.2-1.8 DR/Rb for 300 ppm gas for 10 minutes for gases such as methane, chloromethane and ammonia, as for instance has been previously disclosed by Y. Sakurai et al. in Sensors and Actuators B: Chemical, Vol. 83, No. 1-3, pages 270-275.

More generally, any suitable polymer may be used. An overview of some suitable polymers for use in gas sensors has been provided by Hua Bai et al. in Sensors 2007, Vol. 7, pages 267-307. Another overview of suitable polymers for gas sensor applications is provided by K. Arshak et al. in Sensor Review, 24(2), 2004, pages 181-198.

To enhance the gas or moisture sensitivity of the polymers, at least the portion of the gas or moisture sensitive layer 46 forming part of the gas sensor may be coated with a noble metal such as Pt or Pd. Alternatively, such a noble metal may be dispersed in the polymer. For the interested reader, this is disclosed in more detail in the aforementioned article by Hua Bai et al.; see in particular Table 2 of this article.

In a next step, as shown in FIG. 3(b), the layer 46 of the gas or moisture sensitive material is patterned to finalize the gas or moisture sensor 50 including a portion 46' of the sensitive material and to provide a further portion 46" that acts as a (wavelength) filter for the first photosensitive element 12. The portion 46' and the further portion 46" may still be interconnected or may be separated in the patterning step. The further portion 46" is located on an area of the passivation layer 30 over the first photosensitive element 12 such that the majority of the incident light of the first photosensitive element 12 as indicated by the arrows in FIG. 3(b) passes through the further portion 46". Preferably, substantially all incident light, e.g. at least 90% or even 99% of all incident light of the first photosensitive element 12 passes through the portion 46" of the moisture sensitive material acting as the filter for this photosensitive element.

Although not shown in FIG. 3, it should be understood that a second further portion of the gas or moisture sensitive layer 46 may extend over the reference photosensitive element 12' such that both the $CO_2$-sensitive photosensitive element 12 and the reference photosensitive element 12' are exposed to the same selected, i.e. filtered, part of the electromagnetic spectrum.

In an embodiment, the filter characteristics, i.e. the part of the incident electromagnetic (EM) spectrum absorbed by the portion 46", are governed by the absorption characteristics, i.e. the absorption spectrum of the gas or moisture sensitive material. To this end, the gas or moisture sensitive material may be selected based on the nature of its absorption spectrum to ensure that it can effectively filter out the undesirable part of the EM spectrum. For instance, for a photopic light sensor 12, a material may be selected that strongly absorbs UV and IR irradiation.

In a further embodiment, the absorption spectrum of at least the filter portion 46" of the gas or moisture sensitive material may be tuned by adding a dye to the portion 46". Due to the intense color of dyes, only a small amount of dye may need to be added to the gas sensitive material to alter its absorption spectrum. Any suitable dye may be used. The advantage of having to use only a small amount of dye is that the electrical properties of the gas or moisture sensitive material remain substantially unaffected. This means that the dye may also be present in the portion 46' forming part of the gas or moisture sensor 50, which may simplify application of the dye to the gas or moisture sensitive material.

Figure 4:
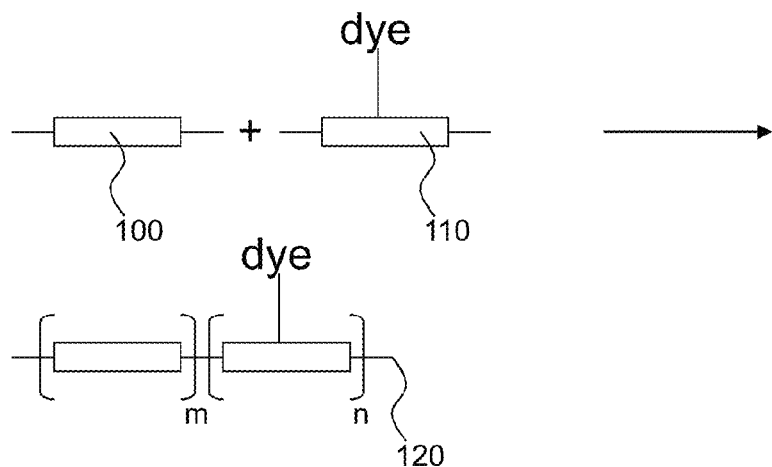

For instance, the dye may be added after the layer 46 of the gas or moisture sensitive material has been deposited over the passivation layer 30, e.g. by absorption of the dye into the layer 46. Alternatively, in case of the gas or moisture sensitive material comprising a polymer, the dye may be incorporated into the polymer. This may for instance be achieved by using two different types of monomers, i.e. a monomer 100 without the dye chemically, e.g. covalently, bound thereto and a monomer 110 comprising the dye, for instance as a substituent, as schematically depicted in FIG. 4, to form a polymer 120 in which the dye is incorporated as a substituent to the polymer backbone. In FIG. 4, m and n are positive integers, with m typically being much larger than n as excess monomer 100 compared to monomer 110 is used in the polymerization reaction. In an embodiment, the ratio of monomer 100: monomer 110 may be at least 10:1, and may be at least 100:1 or even at least 1,000:1. As the chemistry of attaching a dye to a monomer is well-known per se and furthermore highly dependent on the nature of the dye as well as the monomer, this is not explained in further detail for the sake of brevity only.

Upon returning to FIG. 3, the layer portion 14 comprising the organic compound comprising at least one amine or amidine functional group is subsequently formed over the further portion 46'', e.g. by depositing a droplet of a solution including the organic compound and a polymer precursor or a dissolved polymer and subsequently solidifying this layer portion, e.g. by curing or by evaporating the solvent to immobilize the organic compound on the further portion 46'', e.g. in a polymer matrix as previously explained.

It should be understood that the several variations to the IC as shown in FIG. 3c may be contemplated. For instance, the IC may comprise at least four photodiodes 12, with a first photosensitive element not covered by any layer, a second first photosensitive element 12 covered by a moisture-sensitive layer such as a polyimide layer only to provide the relative humidity sensor, a third first photosensitive element 12 covered by the $CO_2$-sensitive layer portion including the organic compound having at least one amine or amidine functional group and a fourth first photosensitive element 12 covered by both the moisture-sensitive layer portion and the $CO_2$-sensitive layer portion, wherein the first photosensitive element may be used to generate a reference signal for the second photosensitive element, and wherein the third photosensitive element may be used to generate a reference signal for the fourth photosensitive element or vice versa. Many other variations will be apparent to the skilled person.

Figure 5:
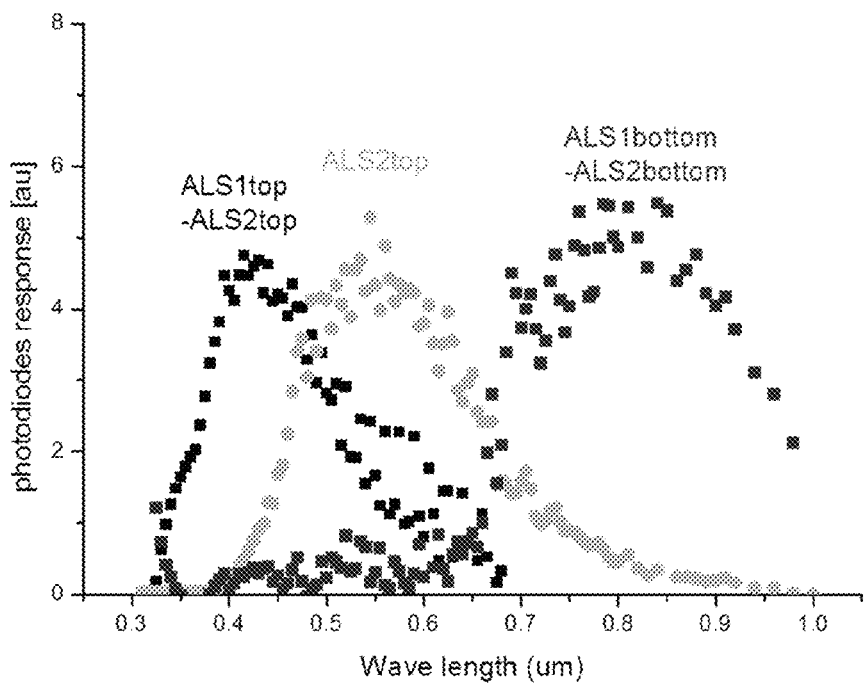
FIG. 5 depicts a measurement result of an IC according to an embodiment of the present invention.

To demonstrate the concept of the filter portion 46'' over the photosensitive element 12, FIG. 5 depicts the results of a measurement performed on a CMOS IC comprising a pair of vertically stacked photosensitive diodes labeled ALS1 and ALS2 in FIG. 3, in which only ALS2 is covered by a polyimide portion, i.e. the area of the passivation layer 20 over ALS2 comprises this portion. It is noted that during these measurements the $CO_2$ sensitive material 14 was omitted for the sake of clarity.

Three measurement curves are depicted in FIG. 5. The curve ALS1top-ALS2top depicts the differential spectrum obtained by subtracting the spectral response of the top diode of ALS2 from the spectral response of the top diode of ALS 1. The curve ALS2top depicts the spectral response of the top diode of ALS2 and the curve ALS1bottom-ALS2bottom depicts the differential spectrum obtained by subtracting the spectral response of the bottom diode of ALS2 from the spectral response of the bottom diode of ALS 1.

As can be seen from curves ALS1top-ALS2top and ALS1bottom-ALS2bottom, a separation of the UV and IR parts of the EM spectrum can be achieved. This can be achieved by simple arithmetic manipulation of the ALS1 and ALS2 signals.

Figure 6:
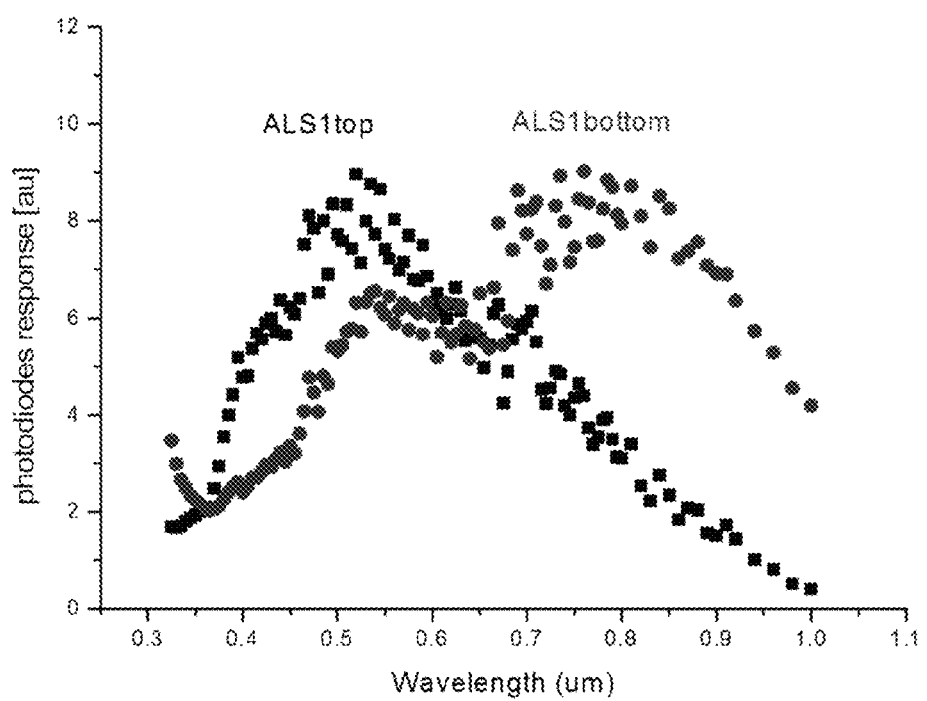
FIG. 6 depicts another measurement result of an IC according to an embodiment of the present invention.

FIG. 6 depicts the spectral response of the (unfiltered) ALS1 top and bottom diode before applying the data extraction shown in FIG. 5. Compared to the response of the ALS2 top diode in FIG. 5 it will be clear that the UV and IR wings of the spectral response of the ALS1 top diode have been effectively suppressed by the polyimide filter portion over the ALS2 top diode.

Figure 7:
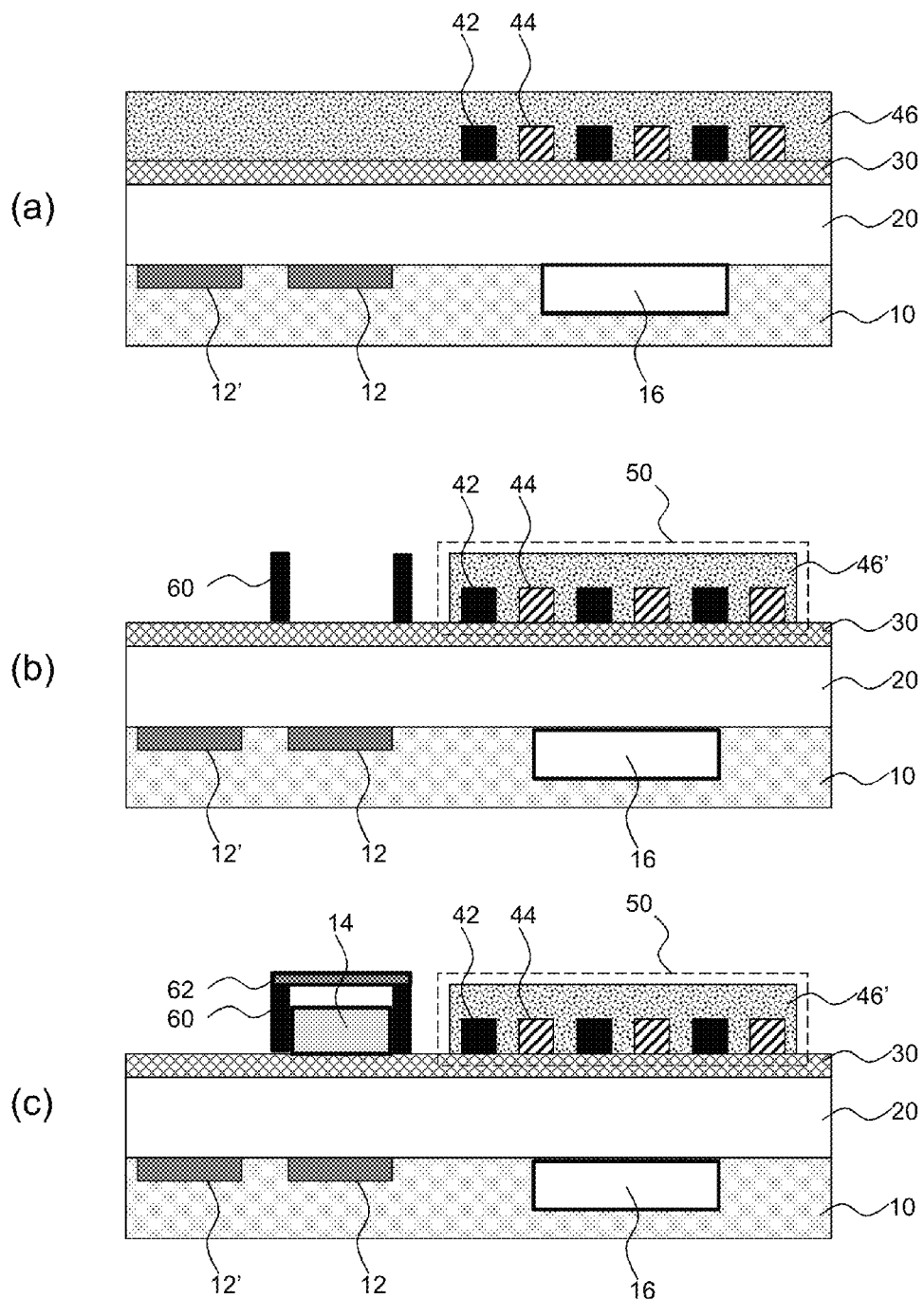
FIG. 7 schematically depicts an IC manufacturing method according to another embodiment of the present invention.

FIG. 7 schematically depicts an alternative embodiment a method of manufacturing an IC in accordance with an embodiment of the present invention. Step (a) is identical to step (a) in FIG. 3 and will not be explained again for the sake of brevity. In step (b), the layer 46 of the gas or moisture sensitive material is patterned to finalize the gas or moisture sensor 50. The difference with the embodiment in FIG. 3 is that the further portion 46'' has been omitted. Instead, a well structure 60 is formed over the first photosensitive element 12, e.g. by spin-coating a polymer such as polyimide over the first photosensitive element 12 and subsequent selective patterning of the polymer into the well structure 60 shown in FIG. 7(b).

Next, as shown in step (c), the organic compound comprising the diamine or amidine functional group is deposited in the well structure 60, e.g. as a neat or dissolved in a suitable solvent, thereby forming a liquid layer portion 14 within the well structure 60. Alternatively, the organic compound may be immobilized in a polymer deposited inside the well structure 60. This may for instance be achieved by depositing a curable mixture inside the well structure 60 and subsequently curing the curable mixture. The well structure 60 is subsequently sealed with a $CO_2$-permeable but liquid-impermeable membrane 62 to retain the liquid layer 14 within the well structure 60.

It is noted that in FIG. 7, a single well 60 is shown by way of non-limiting example only. In alternative embodiments, the well structure may comprise an inner well containing the organic compound 14 and an outer well acting as an anchor for the $CO_2$-permeable membrane 62. In yet another alternative embodiment, an additional well structure may be provided over the second photosensitive element 12', e.g. to place a reference liquid in the additional well structure, such as the solvent used to dissolve the organic compound 14 in the well structure 60. Further suitable variations will be apparent to the skilled person.

It should furthermore be understood that other types of sensors may be added to the IC without departing from the teachings of the present invention. In particular, sensors that can be manufactured using process steps already in use for the manufacturing of the IC are preferred as they do not require a substantial cost increase of the manufacturing process to add such sensors to the IC. An example of a particularly preferable sensor is a temperature sensor such as a PTAT sensor, for which transistor-based implementations are readily available.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An integrated circuit comprising:
   a substrate; and
   an optical $CO_2$ sensor comprising:
   first and second light sensors on said substrate, said second light sensor being spatially separated from the first light sensor; and
   a layer portion including an organic compound comprising at least one amine or amidine functional group for reacting with $CO_2$ over the first light sensor;
   wherein said integrated circuit further comprises a signal processor coupled to the first and second light sensor for determining a difference in the respective outputs of the first and second light sensor.

2. The integrated circuit of claim 1, further comprising a further sensor comprising a pair of electrodes separated by a gas or moisture sensitive material.

3. The integrated circuit of claim 2, wherein the integrated circuit comprises an interconnect structure over the substrate and at least one passivation layer over the interconnect structure, said layer portion and said further sensor being at least partially located on the passivation layer.

4. The integrated circuit of claim 2, wherein the $CO_2$ sensor comprises a further layer portion of the gas or moisture sensitive material over the first light sensor, said organic compound containing layer portion at least partially covering the further layer portion.

5. The integrated circuit of claim 4, wherein the gas or moisture sensitive material comprises a polymer.

6. The integrated circuit of claim 5, wherein the polymer is selected from the group consisting of polyacrylates, polymethacrylates, polyimides, polyamides, polyamines, polypyridines, polycarbonates, polyacetates, polystyrenes, polyacetylenes, polyanilines, polypyrroles, polythiophenes, poly(phenyl vinylene) and derivatives thereof.

7. The integrated circuit of claim 6, wherein the polymer is a polyimide.

8. The integated circuit of claim 4, wherein at least the further layer portion of the moisture sensitive material further comprises a dye.

9. The integrated circuit of claim 1, further comprising a polymer well structure surrounding the first light sensor, wherein the layer portion is contained in the polymer well structure.

10. The integrated circuit of 1, wherein the organic compound is immobilized in a further polymer.

11. An electronic device comprising the integrated circuit of claim 1.

* * * * *